(12) United States Patent
Matsuoka et al.

(10) Patent No.: US 11,959,116 B2
(45) Date of Patent: Apr. 16, 2024

(54) METHOD FOR PRODUCING NICOTINAMIDE MONONUCLEOTIDE

(71) Applicant: Asahi Kasei Pharma Corporation, Tokyo (JP)

(72) Inventors: Takeshi Matsuoka, Tokyo (JP); Tatsuya Hirata, Tokyo (JP); Masaru Yamakoshi, Tokyo (JP)

(73) Assignee: ASAHI KASEI PHARMA CORPORATION, Tokyo (JP)

( * ) Notice: Subject to any disclaimer, the term of this patent is extended or adjusted under 35 U.S.C. 154(b) by 0 days.

(21) Appl. No.: 17/974,381

(22) Filed: Oct. 26, 2022

(65) Prior Publication Data

US 2023/0125968 A1   Apr. 27, 2023

(30) Foreign Application Priority Data

Oct. 27, 2021 (JP) ................. 2021-175812

(51) Int. Cl.
*C12P 19/30* (2006.01)
*C12N 9/10* (2006.01)

(52) U.S. Cl.
CPC ............ *C12P 19/30* (2013.01); *C12N 9/1077* (2013.01); *C12Y 204/02008* (2013.01)

(58) Field of Classification Search
CPC ..................................................... C12P 19/30
See application file for complete search history.

(56) References Cited

U.S. PATENT DOCUMENTS

| | | |
|---|---|---|
| 2008/0299620 A1 | 12/2008 | Park et al. |
| 2017/0121746 A1 | 5/2017 | Velasquez et al. |
| 2017/0304338 A1 | 10/2017 | Dellinger et al. |
| 2018/0162895 A1 | 6/2018 | Fu et al. |
| 2018/0230443 A1 | 8/2018 | Fu et al. |
| 2018/0327797 A1 | 11/2018 | Lawrence et al. |
| 2020/0332332 A1 | 10/2020 | Akiyama |
| 2021/0246476 A1 | 8/2021 | Zhang |
| 2022/0056458 A1 | 2/2022 | Shoji et al. |

FOREIGN PATENT DOCUMENTS

| | | |
|---|---|---|
| CN | 103320373 A | 9/2013 |
| EP | 4 059 571 A1 | 9/2022 |
| JP | 9-215498 A | 8/1997 |
| JP | 2008-543272 A | 12/2008 |
| JP | 2019-501638 A | 1/2019 |
| JP | 2019-514874 A | 6/2019 |
| JP | 2021-151256 A | 9/2021 |
| JP | 2021-176871 A | 11/2021 |
| WO | WO 2017/185549 A1 | 11/2017 |
| WO | WO 2018/023206 A1 | 2/2018 |
| WO | WO 2018/023207 A1 | 2/2018 |
| WO | WO 2018/023208 A1 | 2/2018 |
| WO | WO 2018/023209 A1 | 2/2018 |
| WO | WO 2018/023210 A1 | 2/2018 |
| WO | WO 2019/065876 A1 | 4/2019 |
| WO | WO 2020/129997 A1 | 6/2020 |
| WO | WO 2021/070829 A1 | 4/2021 |

OTHER PUBLICATIONS

Micheli, V., et al. 2002 Biochimica et Biophysica Acta 1587: 45-52. (Year: 2002).*
Karnawat et al., "Differential Distortion of Purine Substrates by Human and Plasmodium falciparum Hypoxanthine-Guanine Phosphoribosyltransferase to Catalyse the Formation of Mononucleotides", ChemPhysChem, May 5, 2015, vol. 16, Issue 10, pp. 2172-2181.
Raman et al., "A non-active site mutation in human hypoxanthine guanine phosphoribosyltransferase expands substrate specificity", Archives of Biochemistry and Biophysics, Jul. 2004, vol. 427, pp. 116-122.
Shen et al., "Biological synthesis of nicotinamide mononucleotide", Biotechnol Lett, Oct. 9, 2021, vol. 43, pp. 2199-2208.
Sugiyama et al., "Nicotinamide mononucleotide production by fructophilic lactic acid bacteria", Scientific Reports, Apr. 2021, vol. 11, No. 7662, pp. 1-8.

* cited by examiner

*Primary Examiner* — Marsha Tsay
(74) *Attorney, Agent, or Firm* — Birch, Stewart, Kolasch & Birch, LLP

(57) ABSTRACT

The present invention addresses the problem of providing a method for producing nicotinamide mononucleotide, that produces nicotinamide mononucleotide using a single enzyme and using nucleoside monophosphate, pyrophosphate, and nicotinamide as starting materials. This problem is solved by a nicotinamide mononucleotide production method that includes at least the following steps 1) and 2): 1) a first step of producing phosphoribosyl diphosphate by the action of substantially one enzyme on nucleoside monophosphate and pyrophosphate; and 2) a second step of producing nicotinamide mononucleotide by the action of only substantially the aforementioned one enzyme on nicotinamide and the phosphoribosyl diphosphate that is the product of the first step.

11 Claims, 2 Drawing Sheets

Specification includes a Sequence Listing.

METHOD FOR PRODUCING NICOTINAMIDE MONONUCLEOTIDE

REFERENCE TO ELECTRONIC SEQUENCE LISTING

The application contains a Sequence Listing which has been submitted electronically in .XML format and is hereby incorporated by reference in its entirety. Said .XML copy, created on Aug. 10, 2023, is named "3939-0329PUS1.xml" and is 25,107 bytes in size. The sequence listing contained in this .XML file is part of the specification and is hereby incorporated by reference herein in its entirety.

BACKGROUND

Field

The present invention relates to a method for producing nicotinamide mononucleotide.

Description of Related Art

Nicotinamide mononucleotide (also referred to as "NMN" in the following) has received attention in recent years as an anti-aging substance, and demand for it as, e.g., a health supplement, has been expanding.

The following methods, inter alia, are known as methods for producing NMN: (1) organic synthesis-based production methods, (2) production methods based on fermentation methods using yeast, and (3) production methods based on enzymatic methods that use enzymes. Of these, organic synthesis-based production methods require a synthesis process that has a number of stages, and as a consequence suffer from the problem of being time-consuming and costly. In addition, fermentation-based production methods exhibit a very poor NMN productivity and require, e.g., large-scale culture equipment.

Several methods are known for the enzyme-based production of NMN. Among these, methods are disclosed in WO 2017/185549, WO 2018/023206, WO 2018/023207, WO 2018/023208, WO 2018/023209, WO 2019/065876, WO 2018/023210, and US Patent Application Publication Nos. 2017/0121746 and 2021/0246476 in which nicotinamide (also referred to as "NAM" in the following) and phosphoribosyl diphosphate (also called phosphoribosyl pyrophosphate) (also referred to as "PRPP" in the following) are converted to NMN by nicotinamide phosphoribosyltransferase (EC 2.4.2.12) (also referred to as "NAMPT" in the following).

Among these methods, WO 2018/023210 and US Patent Application Publication Nos. 2017/0121746 and 2021/0246476 disclose methods in which PRPP is produced using hypoxanthine phosphoribosyltransferase (EC 2.4.2.8) (also referred to as "HGPRT" or "HPT" in the following) from 5'-guanylic acid (GMP) and inosinic acid (IMP) starting materials as inexpensive nucleoside monophosphates, and NMN is produced from this PRPP and NAM as starting materials using NAMPT, that is, methods in which NMN is produced from nucleoside monophosphates using two enzymes, i.e., HGPRT and NAMPT.

SUMMARY

However, a method that produces NMN from nucleoside monophosphate using a single enzyme is unknown.

An object of the present invention is to provide a method for producing nicotinamide mononucleotide, that produces nicotinamide mononucleotide using a single enzyme and using nucleoside monophosphate, pyrophosphate, and nicotinamide as starting materials.

The present inventors discovered a reaction that produces nicotinamide mononucleotide using a single enzyme and using nucleoside monophosphate, pyrophosphate, and nicotinamide as starting materials, and thus achieved the present invention.

The present invention provides the following method for producing nicotinamide mononucleotide in order to achieve the aforementioned object.

[1] A method for producing nicotinamide mononucleotide, that contains at least the following steps 1) and 2):
  1) a first step of producing phosphoribosyl diphosphate by the action of substantially one enzyme on nucleoside monophosphate and pyrophosphate; and
  2) a second step of producing nicotinamide mononucleotide by the action of only substantially the aforementioned one enzyme on nicotinamide and the phosphoribosyl diphosphate that is the product of the first step.

[2] The production method according to [1], wherein the first step and the second step are steps that are carried out simultaneously.

[3] The production method according to [1] or [2], wherein the enzyme is an enzyme belonging to Pentosyltransferases (EC 2.4.2).

[4] The production method according to [3], wherein the enzyme belonging to Pentosyltransferases (EC 2.4.2) is an enzyme belonging to hypoxanthine phosphoribosyltransferase (EC 2.4.2.8).

[5] The production method according to [4], wherein the enzyme belonging to hypoxanthine phosphoribosyltransferase (EC 2.4.2.8) is any of HPT-C, HPT-W, and HPT-L, or is a polypeptide that contains an amino acid sequence that is at least 90% identical with an amino acid sequence in any of HPT-C, HPT-W, and HPT-L.

[6] The production method according to any one of [1] to [5], wherein the nucleoside monophosphate is inosinic acid, guanylic acid, or a mixture of inosinic acid and guanylic acid.

[7] The production method according to any one of [1] to [6], wherein all or a portion of the nucleoside monophosphate is inosinic acid and the first step contains a step of causing the action of xanthine oxidase on the hypoxanthine produced in the first step.

[8] The production method according to any one of [1] to [7], wherein the first step and the second step are steps in which the enzyme acts in the presence of the Mg ion and/or Mn ion.

[9] A method for producing nicotinamide mononucleotide, that produces nicotinamide mononucleotide by the action on phosphoribosyl diphosphate and nicotinamide of one enzyme or a plurality of enzymes belonging to hypoxanthine phosphoribosyltransferase (EC 2.4.2.8).

[10] The production method according to [9], wherein at least one of the enzymes belonging to the hypoxanthine phosphoribosyltransferase (EC 2.4.2.8) is any of HPT-C, HPT-W, and HPT-L, or is a polypeptide that contains an amino acid sequence that is at least 90% identical with an amino acid sequence in any of HPT-C, HPT-W, and HPT-L.

[11] The production method according to [9] or [10], wherein the enzyme acts in the presence of the Mg ion and/or Mn ion.

The present invention can thus provide a method for producing nicotinamide mononucleotide, that produces nicotinamide mononucleotide using a single enzyme and using nucleoside monophosphate, pyrophosphate, and nicotinamide as starting materials.

DETAILED DESCRIPTION

An embodiment for executing the present invention (referred to below as the "present embodiment") is described in detail in the following. The present invention is not limited to or by the embodiment that follows and can be executed making various modifications within the scope of the essential features of the present invention.

Figure 1:
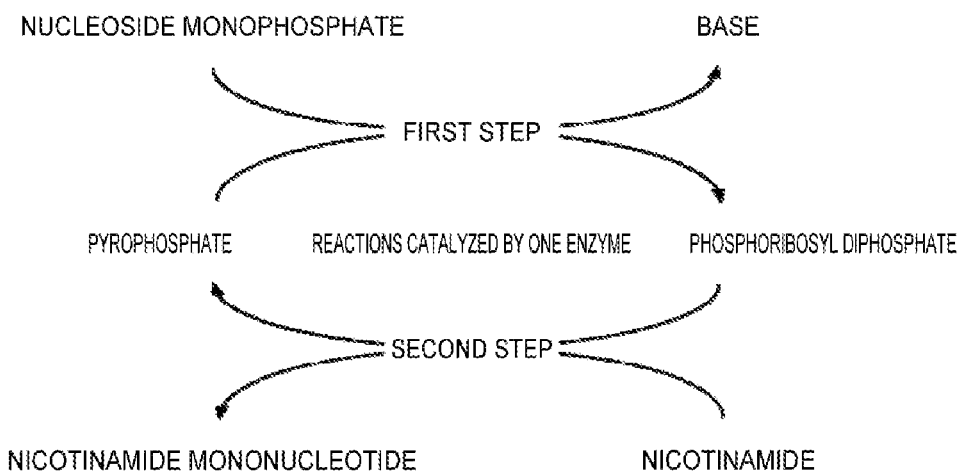
FIG. 1 is a schematic diagram that shows each step in the method for producing nicotinamide mononucleotide according to an embodiment of the present invention.

FIG. 1 is a schematic diagram that shows each step in the method for producing nicotinamide mononucleotide according to the present embodiment.

The method for producing nicotinamide mononucleotide according to the present embodiment contains at least the following steps 1) and 2):

1) a first step of producing phosphoribosyl diphosphate by the action of substantially one enzyme on nucleoside monophosphate and pyrophosphate; and
2) a second step of producing nicotinamide mononucleotide by the action of only substantially the aforementioned one enzyme on nicotinamide and the phosphoribosyl diphosphate that is the product of the first step.

The first step may be carried out prior to the second step, but preferably the first step and the second step are carried out simultaneously. Here, "carried out simultaneously" means that "in the same reactor, the second step is also carried out concurrently while the first step is being carried out".

The nucleoside monophosphate is a type of nucleotide and has the carbon atom at position 1 of a ribose analog (for example, ribose, deoxyribose, and so forth) bonded to a nitrogen atom in a base (for example, a purine base or pyrimidine base) and the carbon atom at position 5 bonded to phosphate group. Examples are AMP, GMP, IMP, XMP, CMP, UMP, OMP, dAMP, dGMP, dCMP, and dTMP.

As noted above, it has already been reported (WO 2018/023210 and US Patent Application Publication Nos. 2017/0121746 and 2021/0246476) that NMN is produced by producing PRPP from pyrophosphate and IMP or GMP, which are nucleoside monophosphates, using an enzyme (the first step in the present Specification) and by bringing about the action of an enzyme on NAM and this PRPP product (the second step in this Specification). HGPRT is taught as the enzyme used in this first step and NAMPT is taught as the enzyme used in the second step (WO 2018/023210 and US Patent Application Publication Nos. 2017/0121746 and 2021/0246476). It is also taught that this first step and second step are carried out simultaneously (Examples 1 to 5 in WO 2018/023210 and Examples 32, 33, and 54 to 56 in US Patent Application Publication No. 2021/0246476).

However, notwithstanding that the first step and second step can be carried out simultaneously, reaction catalysis by a single enzyme is heretofore unknown, and the use of at least two different enzymes has been required. In the enzymatic production of a substance, reducing the number of enzyme types and reducing their amounts are not only very favorable in terms of cost, but also enable a simplification of reaction system control and make a substantial contribution to improving product quality by enabling a simplification of purification of the product post-reaction.

The present inventors unexpectedly discovered that a single enzyme can catalyze the reactions of the first step, in which PRPP is produced from nucleoside monophosphate and pyrophosphate, and the second step, in which NMN is produced from NAM and the PRPP product from the first step, which reactions were heretofore regarded as reactions catalyzed by completely different enzymes. The present inventors thus achieved a method for producing NMN that does not use two enzymes, but, as shown in FIG. 1, that contains a first step and a second step in which the reactions are carried out by one enzyme.

The "one enzyme" referenced here should be an enzyme that can catalyze the reactions of the first step, in which PRPP is produced from nucleoside monophosphate and pyrophosphate, and the second step, in which NMN is produced from NAM and the PRPP product from the first step, and may be a natural enzyme or may be a modified enzyme that has been subjected to, for example, mutation and/or deletion and/or addition and/or fusion, in order to change the reactivity and/or stability and/or specificity. While not being a particular limitation, it can be exemplified by enzymes belonging to Pentosyltransferases (EC 2.4.2). Among these, for example, an enzyme belonging to hypoxanthine phosphoribosyltransferase (EC 2.4.2.8) is preferred. The present Specification also includes enzymes that carry the indicated enzyme number in an older classification, even if they carry a different enzyme number in the current classification.

The "action of one enzyme" indicates that a single enzyme participates through its action in the production reaction, while the presence of another enzyme that in its action does not participate in the production reaction is not excluded. For example, the production of phosphoribosyl diphosphate by the action of one enzyme on nucleoside monophosphate and pyrophosphate also encompasses the participation of a single enzyme in the reaction that produces phosphoribosyl diphosphate from nucleoside monophosphate and pyrophosphate with another enzyme that does not participate in this reaction also being present.

The "substantially one enzyme" indicates that one enzyme is at least 90% and other admixed enzyme is not more than 10%, wherein preferably one enzyme is at least 95% and other admixed enzyme is not more than 5% and more preferably one enzyme is at least 99% and other admixed enzyme is not more than 1%. In addition, the % indication used here for the enzymes may be any % indication using the enzyme protein weight or a unit that is an activity unit for the enzyme. The other admixed enzyme is a single enzyme or a plurality of enzymes that can catalyze the reaction in the first step and/or the second step.

Favorable examples of the enzyme belonging to hypoxanthine phosphoribosyltransferase (EC 2.4.2.8) are the "HPT-W (named by the present inventors)" enzyme comprising the amino acid sequence given by SEQ ID NO: 4, the "HPT-C (named by the present inventors)" enzyme comprising the amino acid sequence given by SEQ ID NO: 7, and the "HPT-L (named by the present inventors)" enzyme comprising the amino acid sequence given by SEQ ID NO: 11. Additional examples are polypeptides that contain an amino acid sequence that is at least 70%, or at least 80%, or at least 90%, or at least 95%, or at least 98% identical with the aforementioned amino acid sequences.

While WO 2018/023210 and US Patent Application Publication Nos. 2017/0121746 and 2021/0246476 disclose NMN production methods that use two enzymes, i.e., HGPRT and NAMPT, and use NAM, IMP or GMP, and pyrophosphate as starting materials, the existence of an enzyme having both HGPRT activity and NAMPT activity is not suggested, nor is there recognition of the discovery and/or development of such an enzyme as a problem. Thus, even combining the heretofore disclosed prior art, there has to date been no suggestion whatever with regard to an NMN production method that contains a first step and a second step in which the reactions are carried out by one enzyme.

In particular, the length of the peptide of hypoxanthine phosphoribosyltransferase (EC 2.4.2.8) is approximately 200 amino acids and the length of the peptide of nicotinamide phosphoribosyltransferase (EC 2.4.2.12) is approximately 450 amino acids, which are very different from a structural standpoint, and as a consequence there has heretofore also been no expectation that hypoxanthine phosphoribosyltransferase (EC 2.4.2.8) would have the same or similar activity for nicotinamide as nicotinamide phosphoribosyltransferase (EC 2.4.2.12).

The conditions in the steps in the nicotinamide mononucleotide production method according to the present embodiment that contains at least the aforementioned first step and the aforementioned second step, can be designed and optimized in order to efficiently produce nicotinamide mononucleotide.

This efficient production is production that brings about an increase in, for example, the amount and purity of the recovered product, relative to the amount of charged starting materials and enzyme, time, workload, operational safety, and impact on the environment. In particular, since the first step and the second step are also equilibrium reactions, the design and optimization of the conditions in the steps in order to shift the equilibrium in a desirable direction, such as increasing the amount of product, is crucial for the efficient production of nicotinamide mononucleotide.

Optimization of the conditions in the steps, which is described in detail below, concerns, for example, the following: the type of enzyme, the enzyme formulation, the enzyme concentration, the type of substrate starting materials, the concentrations and ratios for the substrate starting materials, the reaction temperature, the reaction time, the dissolved oxygen concentration, pH, the buffer type and its concentration, adjustment of the ionic strength, addition of enzyme stabilizers, addition of product stabilizers, addition of surfactant, addition of organic solvent, addition of reaction cofactors and/or addition of reaction-promoting components, and removal of by-products.

Optimization of the type of enzyme refers to the selection, from the group of enzymes that can catalyze the reactions of the first step and the second step, of a favorable species of enzyme in conformity to the type of substrate starting materials in order to efficiently produce nicotinamide mononucleotide. For example, optimization can be carried out by selecting an enzyme that belongs to the Pentosyltransferases (EC 2.4.2). In addition, optimization can be carried out by selection, from among enzymes belonging to Pentosyltransferases (EC 2.4.2), of an enzyme belonging to any of the following: purine-nucleoside phosphorylase (EC 2.4.2.1), pyrimidine-nucleoside phosphorylase (EC 2.4.2.2), uridine phosphorylase (EC 2.4.2.3), thymidine phosphorylase (EC 2.4.2.4), nucleoside ribosyltransferase (EC 2.4.2.5), nucleoside deoxyribosyltransferase (EC 2.4.2.6), adenine phosphoribosyltransferase (EC 2.4.2.7), hypoxanthine phosphoribosyltransferase (EC 2.4.2.8), uracil phosphoribosyltransferase (EC 2.4.2.9), orotate phosphoribosyltransferase (EC 2.4.2.10), nicotinate phosphoribosyltransferase (EC 6.3.4.21, old enzyme number: EC 2.4.2.11), nicotinamide phosphoribosyltransferase (EC 2.4.2.12), methionine adenosyltransferase (EC 2.5.1.6, old enzyme number: EC 2.4.2.13), am idophosphoribosyltransferase (EC 2.4.2.14), guanosine phosphorylase (EC 2.4.2.15), urate-ribonucleoside phosphorylase (EC 2.4.2.16), ATP phosphoribosyltransferase (EC 2.4.2.17), anthranilate phosphoribosyltransferase (EC 2.4.2.18), nicotinate-nucleotide diphosphorylase (carboxylating) (EC 2.4.2.19), dioxotetrahydropyrimidine phosphoribosyltransferase (EC 2.4.2.20), nicotinate-nucleotide-dimethylbenzimidazole phosphoribosyltransferase (EC 2.4.2.21), xanthine phosphoribosyltransferase (EC 2.4.2.22), deoxyuridine phosphorylase (EC 2.4.2.2, EC 2.4.2.3, EC 2.4.2.4., old enzyme number: EC 2.4.2.23), 1,4-beta-D-xylan synthase (EC 2.4.2.24), flavone apiosyltransferase (EC 2.4.2.25), protein xylosyltransferase (EC 2.4.2.26), dTDP-dihydrostreptose-streptidine-6-phosphate dihydrostreptosyltransferase (EC 2.4.2.27), S-methyl-5'-thioadenosine phosphorylase (EC 2.4.2.28), tRNA-guanosine34 transglycosylase (EC 2.4.2.29), NAD$^+$ ADP-ribosyltransferase (EC 2.4.2.30), NAD$^+$-protein-arginine ADP-ribosyltransferase (EC 2.4.2.31), dolichyl-phosphate D-xylosyltransferase (EC 2.4.2.32), dolichyl-xylosyl-phosphate-protein xylosyltransferase (EC 2.4.2.33), indolylacetylinositol arabinosyltransferase (EC 2.4.2.34), flavonol-3-O-glycoside xylosyltransferase (EC 2.4.2.35), NAD$^+$-diphthamide ADP-ribosyltransferase (EC 2.4.2.36), NAD$^+$-dinitrogen-reductase ADP-D-ribosyltransferase (EC 2.4.2.37), glycoprotein 2-beta-D-xylosyltransferase (EC 2.4.2.38), xyloglucan 6-xylosyltransferase (EC 2.4.2.39), zeatin O-beta-D-xylosyltransferase (EC 2.4.2.40), xylogalacturonan beta-1,3-xylosyltransferase (EC 2.4.2.41), UDP-D-xylose:beta-D-glucoside alpha-1,3-D-xylosyltransferase (EC 2.4.2.42), lipid IVA 4-amino-4-deoxy-L-arabinosyltransferase (EC 2.4.2.43), S-methyl-5'-thioinosine phosphorylase (EC 2.4.2.44), decaprenyl-phosphate phosphoribosyltransferase (EC 2.4.2.45), galactan 5-O-arabinofuranosyltransferase (EC 2.4.2.46), arabinofuranan 3-O-arabinosyltransferase (EC 2.4.2.47), tRNA-guanine15 transglycosylase (EC 2.4.2.48), neamine phosphoribosyltransferase (EC 2.4.2.49), cyanidin 3-O-galactoside 2"-O-xylosyltransferase (EC 2.4.2.50), anthocyanidin 3-O-glucoside 2'"-O-xylosyltransferase (EC 2.4.2.51), triphosphoribosyl-dephospho-CoA synthase (EC 2.4.2.52), undecaprenyl-phosphate 4-deoxy-4-formamido-L-arabinose transferase (EC 2.4.2.53), beta-ribofuranosylphenol 5'-phosphate synthase (EC 2.4.2.54), nicotinate D-ribonucleotide: phenol phospho-D-ribosyltransferase (EC 2.4.2.55), kaempferol 3-O-xylosyltransferase (EC 2.4.2.56), AMP phosphorylase (EC 2.4.2.57), hydroxyproline 0-arabinosyltransferase (EC 2.4.2.58), sulfide-dependent adenosine diphosphate thiazole synthase (EC 2.4.2.59), cysteine-dependent adenosine diphosphate thiazole synthase (EC 2.4.2.60), alpha-dystroglycan beta-1,4-xylosyltransferase (EC 2.4.2.61), xylosyl alpha-1,3-xylosyltransferase (EC 2.4.2.62), EGF-domain serine xylosyltransferase (EC 2.4.2.63), NAD$^+$-protein-arginine ADP-ribosyltransferase (EC 2.4.2.612), NAD$^+$-protein-arginine ADP-ribosyltransferase (EC 2.4.2.613), and (KDO)2-lipid IV(A) 4-amino-4-deoxy-L-arabinosyltransferase (EC 2.4.2.64). Optimization can also be carried out by selection of a hypoxanthine phosphoribosyltransferase (EC 2.4.2.8) derived from any of *Archaeoglobus* veneficus, Artemia sp., *Bos taurus, Caldanaerobacter subterraneus* subsp. *tengcongensis, Carboxydothermus hydrogenoformans, Cricetulus griseus, Cryptosporidium parvum, Escherichia coli, Gallus gallus,* Giardia intestinalis, Giardia intestinalis Portland, *Halobacterium salinarum, Haloferax volcanii, Homo sapiens, Hungateiclostridium thermocellum, Hungateiclostridium thermocellum* DSM 1237, *Legionella pneumophila, Leishmania donovani, Leishmania tarentolae,* Lontra longicaudis, Methanococcus voltae, Mirounga angustirostris, *Mus musculus, Mycobacterium tuberculosis, Mycobacterium tuberculosis* H37Rv, *Plasmodium* chabaudi, *Plasmodium falciparum, Plasmodium lophurae, Pyrococcus horikoshii, Rattus norvegicus, Saccharolobus solfataricus, Saccharolobus solfataricus* P2, *Saccharomyces cerevisiae, Salmonella enterica* subsp. *enterica* serovar *Typhimurium, Salmonella enterica* subsp. *enterica* serovar *Typhimurium* LT2, *Schistosoma mansoni, Schizosaccharomyces pombe, Streptomyces cyanogenus, Sus scrofa, Thermus thermophilus, Thermus thermophilus* HB8/ATCC 27634/DSM 579, *Toxoplasma gondii, Tritrichomonas suis,* and *Trypanosoma cruzi*. In addition, optimization can be carried out by selecting the aforementioned enzymes as such or by selecting any enzyme produced by, for example, a genetically recombinant organism, as a modified enzyme provided by, e.g., deletion, insertion, addition, fusion, and so forth, in the amino acid sequence. When selection is made from any of the aforementioned HPT-W, HPT-C, and HPT-L, those produced as described in the following examples are preferred, but selection may be made from those produced from other genetically recombinant microorganisms.

When the nucleoside monophosphate that is a starting substrate is IMP, GMP, or their mixture, an enzyme belonging to any of hypoxanthine phosphoribosyltransferase (EC 2.4.2.8), nicotinate phosphoribosyltransferase (EC 6.3.4.21), and nicotinamide phosphoribosyltransferase (EC 2.4.2.12) is preferably selected.

When the nucleoside monophosphate that is a starting substrate is AMP or incorporates same, an enzyme belonging to any of adenine phosphoribosyltransferase (EC 2.4.2.7), nicotinate phosphoribosyltransferase (EC 6.3.4.21), and nicotinamide phosphoribosyltransferase (EC 2.4.2.12) is preferably selected.

When the nucleoside monophosphate that is a starting substrate is UMP or incorporates same, an enzyme belonging to any of uracil phosphoribosyltransferase (EC 2.4.2.9), nicotinate phosphoribosyltransferase (EC 6.3.4.21), and nicotinamide phosphoribosyltransferase (EC 2.4.2.12) is preferably selected.

When the nucleoside monophosphate that is a starting substrate is OMP or incorporates same, an enzyme belonging to any of orotate phosphoribosyltransferase (EC 2.4.2.10), nicotinate phosphoribosyltransferase (EC 6.3.4.21), and nicotinamide phosphoribosyltransferase (EC 2.4.2.12) is preferably selected.

When the nucleoside monophosphate that is a starting substrate is XMP or incorporates same, an enzyme belonging to any of xanthine phosphoribosyltransferase (EC 2.4.2.22), nicotinate phosphoribosyltransferase (EC 6.3.4.21), and nicotinamide phosphoribosyltransferase (EC 2.4.2.12) is preferably selected.

Optimization of the enzyme formulation refers to the selection of the optimal enzyme formulation for the respective conditions from, e.g., viable microorganisms that contain the enzyme, inactivated microorganisms that contain the enzyme, a crude extract material or crude extract liquid from an enzyme-containing microorganism, powdered enzyme or liquid enzyme provided by a purification process, enzyme that has been polymerized using a polymerizing agent such as a linker, enzyme that has been immobilized on a carrier such as polystyrene, acrylamide, or agarose, and so forth. In addition, the carrier bearing the immobilized enzyme may be packed in a column and the reaction solution for the step may be passed through or circulated through.

Optimization of the enzyme concentration refers to the selection—while also considering the various other conditions—of the optimal concentration for the enzyme concentration acting on the nucleoside monophosphate and pyrophosphate and the enzyme concentration acting on the PRPP reaction product and NAM. For the enzyme protein concentration, optimization can be carried out by selection of a favorable concentration from the range of, for example, 0.001 mg to 100 g/L, preferably 1 mg to 100 g/L, and more preferably 1 to 100 g/L; for the activity concentration of the enzyme, optimization can be carried out by selection of a favorable concentration from the range of, for example, 0.01 U to 1000 kU/L, preferably 1 U to 100 kU/L, and more preferably 10 U to 10 kU/L.

Optimization of the type of substrate starting materials refers to the selection—while also considering the various other conditions—of optimal nucleoside monophosphate, which should produce PRPP by the enzymatic reaction using the nucleoside monophosphate as a substrate starting material and which may be exemplified by IMP, GMP, AMP, UMP, OMP, XMP, and mixtures of two or more of these. In addition, for the nucleoside monophosphate, pyrophosphate, and NAM, optimization can be carried out—while also considering the various other conditions—by the selection of a starting material residing in an optimal state, which should be the state at the time of reaction with the enzyme in the reaction solution in the particular step and which can be exemplified, at the time of introduction as starting material, by a salt of the preceding, e.g., sodium salt, potassium salt, and ammonium salt, and/or a hydrate.

Optimization of the concentrations and ratios for the substrate starting materials refers to selection—while also considering the various other conditions—of the optimal concentrations and ratios therebetween for the nucleoside monophosphate and pyrophosphate in the reaction solution at the start of the first step, and to the optimization—while also considering the various other conditions—of the concentrations and ratios thereamong for the nucleoside monophosphate, pyrophosphate, and NAM in the reaction solution at the start of the second step. For the concentrations and ratios therebetween in the reaction solution at the start of the first step, favorable values are selected, for example, from the range of 0.01 to 500 mM and preferably 0.1 to 20 mM for the nucleoside monophosphate concentration and from the range of 0.001 to 100 mM and preferably 0.02 to 10 mM for the pyrophosphate concentration, and, for example, from the range of 1:0.001 to 100 for the ratio between the nucleoside monophosphate and pyrophosphate concentrations. For the concentrations and ratios thereamong in the reaction solution at the start of the second step, favorable values are selected, for example, from the range of 0 to 500 mM and preferably 0.1 to 20 mM for the nucleoside monophosphate concentration, from the range of 0 to 100 mM for the pyrophosphate concentration, and from the range of 0.01 to 500 mM and preferably 0.1 to 20 mM for the NAM concentration, and, for example, from the range of 0 to 10:0 to 100:1 for the ratios among the nucleoside monophosphate, pyrophosphate, and NAM concentrations. For example, when the first step and the second step are started at the same time and IMP is used for the nucleoside monophosphate, favorable values are selected from the range of 0.1 to 10:0.001 to 100:1 for the ratios among the IMP, pyrophosphate, and NAM concentrations. In addition, optimization may also be carried out by changing the substrate starting material concentrations and ratios during the course of a step by carrying out concentration, dilution, or the supplemental addition of a starting material.

Optimization of the reaction temperature refers to optimization—while also considering the various other conditions—in particular of the temperature in each step when the first step is carried out prior to the second step, or the temperature of the step provided when the first step and the second step are performed simultaneously. For example, a constant temperature or in-process variation can be investigated in the range of 0 to 70° C. and preferably 25 to 65° C., and optimization can be carried out by selecting the optimal temperature or optimal temperature change program.

Optimization of the reaction time refers to optimization—while also considering the various other conditions—in particular of the time in each step when the first step is carried out prior to the second step, or the time of the step provided when the first step and the second step are performed simultaneously. For example, optimization can be carried out by selection from the range of 1 to 240 hours and preferably 1 to 72 hours.

Optimization of the dissolved oxygen concentration refers to the optimization—while also considering the various other conditions—in particular of the oxygen concentration in the reaction solution in each step when the first step is carried out prior to the second step, or the oxygen concentration in the reaction solution of the step provided when the first step and the second step are performed simultaneously. For example, in-process variations or a constant in-process concentration can be investigated in the range of 0 to 14.15 mg/L, and optimization can be carried out by selecting the optimal concentration or optimal concentration variation program.

Optimization of the pH refers to optimization—while also considering the various other conditions—in particular of the pH in the reaction solution in each step when the first step is carried out prior to the second step, or the pH in the reaction solution of the step provided when the first step and the second step are performed simultaneously. For example, in-process variations or a constant in-process pH can be investigated in the pH range from 4 to 11, and optimization can be carried out by selecting the optimal pH or optimal pH conditioning program.

Optimization of the buffer type and its concentration refers to optimization by selection—while also considering the various other conditions—in particular of the buffer type and its concentration in each step when the first step is carried out prior to the second step, or the buffer type and its concentration in the step provided when the first step and the second step are performed simultaneously. Optimization can be carried out by selection of the optimal concentration from the range of buffer concentrations from 1 to 500 mM, and, with regard to the buffer type, by selection of the optimal type from, for example, citrate buffers, tartrate buffers, acetate buffers, carbonate buffers, phosphate buffers, borate buffers, Good's buffers, Tris buffers, Bis-Tris buffers, ammonium buffers, triethylamine buffers, glycine buffers, McIlvaine buffers, and buffers comprising a combination of the preceding.

Optimization of the adjustment of the ionic strength refers to the execution—while also considering the various other conditions—in particular of adjustment of the ionic strength in each step when the first step is carried out prior to the second step, or adjustment of the ionic strength in the step provided when the first step and the second step are performed simultaneously. The method for adjusting the ionic strength can be exemplified by adjustment of the buffer concentration in the reaction solution or the addition of a salt, e.g., NaCl, KCl, $(NH_4)_2SO_4$, and so forth, to the reaction solution, while optimization can be carried out by establishing an optimal ionic strength by selecting a buffer concentration in the range from 1 to 500 mM or an NaCl concentration in the range from 0 to 2 M, a KCl concentration in the range from 0 to 2 M, or an $(NH_4)_2SO_4$ concentration in the range from 0 to 1 M.

Optimization of the addition of enzyme stabilizers refers to the addition to the reaction solution of the first step or the second step—with selection of the type and concentration while also considering the various other conditions—of an enzyme stabilizer for maintaining enzyme activity during the step. Optimization can be carried out, for example, by the addition to the reaction solution as an enzyme stabilizer of NaCl, KCl, or $(NH_4)_2SO_4$ with selection of the concentration in the range from 0.1 to 0.5 M; or glycerol, ethylene glycol, sucrose, trehalose, sorbitol, mannitol, or ethanol with selection of the concentration in the range from 0.1 to 50%; or surfactant, skim milk, soy protein, whey, casein, or albumin with selection of the concentration in the range from 0.001 to 1%.

Optimization of the addition of product stabilizers refers to the addition—with selection of the type and concentration while also considering the various other conditions—of product stabilizers to the reaction solution in the first step or the second step, in order to prevent yield reductions due to unexpected decomposition of the product in the first step and the product in the second step due to, e.g., heat, oxygen, admixed substances, admixed enzyme, and so forth. Optimization can be carried out, for example, by a suitable selection of product stabilizers from, e.g., sodium sulfite, catalase, chelating agents such as EDTA, and reducing agents such as mercaptoethanol, DTT, and thioglycerol, and the addition of same to the reaction solution.

Optimization of the addition of surfactant refers to the addition—with selection of the type and concentration while also considering the various other conditions—of a surfactant to the reaction solution in the first step or the second step, in order to promote the enzymatic reaction of the first step or the second step and shift the reaction equilibrium so as to increase the amount of product. Optimization can be carried out, for example, by the addition to the reaction solution of a suitable surfactant selection from anionic surfactants, cationic surfactants, amphoteric surfactants, nonionic surfactants, saponins, phospholipids, peptides, and biosurfactants (glycolipids, acylpeptides, phospholipids, fatty acids, and polymers).

Optimization of the addition of organic solvent refers to the addition—with selection of the type and concentration while also considering the various other conditions—of an organic solvent to the reaction solution in the first step or the second step, in order to promote the enzymatic reaction of the first step or the second step and shift the reaction equilibrium so as to increase the amount of product. Optimization can be carried out, for example, by the addition to the reaction solution of a suitable organic solvent selection from methanol, ethanol, isopropyl alcohol, hexane, and so forth.

Optimization of the addition of reaction cofactors and/or addition of reaction-promoting components refers to the addition—with selection of the type and concentration while also considering the various other conditions—of a cofactor required for the enzymatic reaction in the first step or the second step, and/or a reaction cofactor or reaction-promoting component to the reaction solution in the first step or the second step in order to activate the reaction and thereby shorten the reaction time and/or reduce the amount of enzyme addition. Optimization can be carried out, for example, by the addition to the reaction solution, in the range of, e.g., 0.001 to 100 mM, preferably 0.1 to 100 mM, and more preferably 2 to 50 mM, of a suitable reaction cofactor or reaction-promoting component, or combination thereof, selected from, e.g., Mg compounds such as $MgCl_2$ and $MgSO_4$, Mn compounds such as $MnCl_2$, Fe compounds such as $FeCl_3$ and $FeCl_2$, Zn compounds such as $ZnCl_2$, Co compounds, Mo compounds, Cu compounds, Ag compounds, Al compounds, Ca compounds, and Ni compounds.

Optimization of the removal of by-products refers to selection—while also considering the various other conditions—of the conditions for removal of the base from the reaction solution in the first step and the pyrophosphate from the reaction solution in the second step. When the nucleoside monophosphate in the first step is IMP, this concerns the removal of hypoxanthine; when the nucleoside monophosphate is GMP, this concerns the removal of guanine; and when the nucleoside monophosphate is AMP, this concerns the removal of adenine.

Hypoxanthine can be removed by conversion to xanthine and uric acid using xanthine oxidase or xanthine dehydrogenase. In the case of use of xanthine oxidase, hypoxanthine can be more efficiently removed by removal of the produced hydrogen peroxide using catalase or peroxidase. In the case of use of xanthine dehydrogenase, hypoxanthine can be more efficiently removed by conversion of the produced NADH to NAD using, for example, NADH oxidase. In the case of xanthine oxidase, XTO-212 (code name) from Toyobo Co., Ltd. can be added at an enzyme concentration of 0.01 to 100 U/mL and preferably 0.1 to 10 U/mL, and the aforementioned conversion reaction may be carried out at a reaction temperature of 0 to 70° C. and preferably of 25 to 65° C.

Guanine removal can be accomplished by conversion of the guanine to xanthine using guanine deaminase followed by removal of the xanthine.

Adenine removal can be accomplished by conversion of the adenine to hypoxanthine using adenine deaminase followed by removal of the hypoxanthine.

In addition, since hypoxanthine, guanine, and adenine all have low water solubilities, removal may be carried out by repeating the following: reaction at high temperatures followed by cooling and precipitation, removal by centrifugal separation and/or filtration, and then return to high temperatures. For example, this may be performed using the range of 37 to 65° C. for the high temperature and using 0 to 10° C. for cooling. Moreover, since hypoxanthine, guanine, and adenine all having low water solubilities, removal may be carried out by repeating the following: concentration, e.g., by distilling the water, and precipitation, separation by centrifugal separation and/or filtration, followed by the fresh addition of water to restart. Removal may also be carried out by extraction into an organic solvent, e.g., hexane or chloroform, and layer separation. Removal may also be carried out by adsorbing the hypoxanthine, guanine, or adenine to, for example, a resin.

When the nucleoside monophosphate in the first step is a mixture of IMP and GMP, a suitable combination of the methods listed above may be used.

The pyrophosphate produced in the second step may be simply removed when the first step is carried out prior to the second step; however, when the first step and the second step are performed simultaneously, removal must be carried out after the first step has developed to a satisfactory degree. This satisfactory development of the first step means, for example, that base has been produced from at least 10% of the nucleoside monophosphate charged as starting material and preferably from at least 30%, more preferably from at least 50%, still more preferably from at least 70%, and most preferably from at least 90%.

The pyrophosphate can be removed, for example, by the following methods: addition of, for example, inorganic diphosphatase (EC 3.6.1.1) to the reaction solution and execution of hydrolysis to phosphate; precipitation by the addition of a cation (for example, precipitation caused by the addition of excess Mg ion, Mn ion, or Ca ion). The addition of excess Mg ion, Mn ion, or Ca ion indicates the addition to the reaction solution of an Mg compound, Mn compound, or Ca compound in an excess concentration of at least 50 mM, preferably at least 100 mM, more preferably at least 200 mM, still more preferably at least 500 mM, and most preferably at least 1,000 mM. The pyrophosphate may also be removed by adsorption to, for example, a resin.

The present embodiment can thus provide a nicotinamide mononucleotide production method that produces nicotinamide mononucleotide using one enzyme and using nucleoside monophosphate, pyrophosphate, and nicotinamide as starting materials. The present embodiment can thus provide a nicotinamide mononucleotide production method that produces nicotinamide mononucleotide using a simple process from a small number of relatively inexpensive starting materials.

Another embodiment can provide a nicotinamide mononucleotide production method that produces nicotinamide mononucleotide by causing the action on phosphoribosyl diphosphate and nicotinamide of an enzyme belonging to hypoxanthine phosphoribosyltransferase (EC 2.4.2.8). When this production method is used in the production method according to the previously described present embodiment comprising the first and second steps as described in the preceding, the reaction-mediating enzyme belonging to hypoxanthine phosphoribosyltransferase (EC 2.4.2.8) is one enzyme (including the previously described case of substantially one); however, in other cases, for example, in the case of carrying out a production method composed of only the second step, it may be a plurality of enzymes. For example, the reaction may be carried out using two or more enzymes selected from HPT-C, HPT-W, HPT-L, and polypeptides containing an amino acid sequence that is at least 90% identical with an amino acid sequence in HPT-C, HPT-W, or HPT-L. The substantially one enzyme is as described above, while here one enzyme or a plurality of enzymes is or are an enzyme or enzymes belong to hypoxanthine phosphoribosyltransferase (EC 2.4.2.8) and additional admixed enzyme is one or a plurality of enzymes that can catalyze the aforementioned nicotinamide mononucleotide production reaction (corresponds to the second step). Also in the case of reaction with one or a plurality of enzymes belonging to hypoxanthine phosphoribosyltransferase (EC 2.4.2.8), the additional admixed enzyme may be admixed at not more than 10%, preferably not more than 5%, and more preferably not more than 1% of the total enzyme catalyzing the aforementioned reaction. Moreover, additional enzyme that does not catalyze the aforementioned nicotinamide mononucleotide production reaction (corresponds to the second step) may be co-present in addition to the one or plurality of enzymes belonging to hypoxanthine phosphoribosyltransferase (EC 2.4.2.8).

Examples of the present invention are described in detail in the following, but the present invention is in no way limited to or by these.

EXAMPLES

Example 1: Detection Using HPLC of Bases, Nucleoside Monophosphates, Nicotinamide, and Nicotinamide Mononucleotide Preparation of Sample Solutions Sample solutions were prepared by dissolving the following samples in purified water to provide the indicated concentrations.

| | |
|---|---|
| 0.05 mg/mL | IMP |
| 0.05 mg/mL | GMP |
| 0.05 mg/mL | NMN |
| 0.02 mg/mL | hypoxanthine |
| 0.02 mg/mL | guanine |
| 0.02 mg/mL | NAM |

Figure 2:
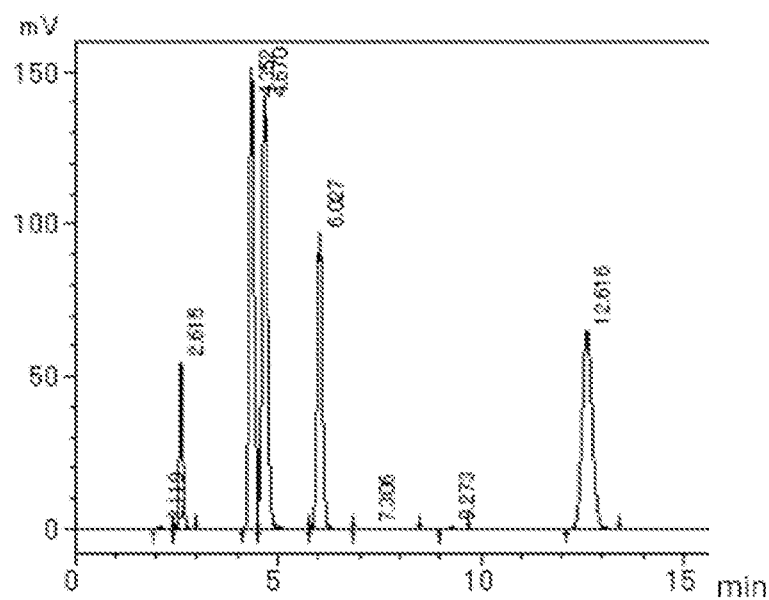
FIG. 2 is a diagram that shows the HPLC elution behavior of the sample in Example 1.

Detection Conditions
HPLC system: Shimadzu LC-20A
detection: UV, 254 nm
column: YMC-Triart C18
TA12S05-1546WT 150 mm×4.6 mm (YMC Co., Ltd., Japan) flow rate, mode, column temperature: 1 mL/min, isocratic, 37° C. mobile phase: 10 mM potassium dihydrogenphosphate sample injection: 5 μL Results The results are given in FIG. 2 and Table 1. FIG. 2 shows the elution behavior (horizontal axis: elution time (min), vertical axis: detection intensity (mV)). The retention times for the individual samples are given in Table 1, which demonstrate peak separation except for hypoxanthine and guanine.

TABLE 1

| sample | retention time (min) |
|---|---|
| NMN | 2.615 |
| GMP | 4.352 |
| IMP | 4.670 |
| hypoxanthine | 6.027 |
| guanine | 6.027 |
| NAM | 12.616 |

Example 2: Production of HGPRT (1) Preparation of Transformant with Plasmid into which E. coli-Derived HGPRT has been Inserted
(1.1) Confirmation of Sequence of E. coli-Derived HGPRT Using chromosomal DNA from Escherichia coli strain W3110 as the template, PCR was carried out using a sense primer (SEQ ID NO: 1), an antisense primer (SEQ ID NO: 2), and KOD PLUS NEO (product number: KOD-401, Toyobo Co., Ltd.) to amplify the HGPRT gene and obtain a PCR product. The resulting PCR product was inserted into pCR-Blunt II-Topo (Thermo Fisher Scientific Inc.) using a Zero Blunt TOPO PCR cloning kit, followed by confirmation of the base sequence of the resulting PCR product by sequencing. The confirmed base sequence of the HGPRT derived from Escherichia coli strain W3110 and the amino acid sequence presumed from this base sequence are in SEQ ID NO: 3 and SEQ ID NO: 4, respectively.

(1.2) Preparation of Transformant with Plasmid into which E. coli-Derived HGPRT has been Inserted Using as template the pCR-Blunt II-Topo carrying the E. coli-derived HGPRT gene, PCR was carried out using a sense primer (SEQ ID NO: 5), an antisense primer (SEQ ID NO: 6), and KOD PLUS NEO (product number: KOD-401, Toyobo Co., Ltd.) to obtain a PCR product in which the HGPRT gene having each of the following was amplified: the sequence AAGGAGATATACAT (SEQ ID NO: 15) prior to the start codon at the 5'-terminal, the His tag-encoding CATCACCATCACCATCAC (SEQ ID NO: 16) sequence immediately after the HGPRT start codon, and the GGATCCGAATTCGAGC (SEQ ID NO: 17) sequence immediately after the stop codon on the 3'-terminal side. Using an In-Fusion HD Cloning Kit (Takara Bio Inc.), the resulting PCR product was inserted by the In-Fusion method into the NdeI-BamHI site of the pET-21a(+) vector (Novagen, Inc.), which is an expression vector, to yield an HGPRT/pET21a(+) expression plasmid. This expression plasmid had the His tag-encoding base sequence added to the 5'-terminal of the HGPRT gene. This expression plasmid was introduced into One Shot BL21(DE3) Chemically Competent E. coli (Invitrogen Corporation) to obtain an HGPRT/pET-21a(+)/BL21(DE3) transformant having a recombinant vector that contained polynucleotide coding for E. coli-derived HGPRT.

(2) Preparation of E. coli-Derived HGPRT (HPT-W)
(2.1) Induction of HGPRT Expression by the Transformant and Preparation of Crude Enzyme Solution One colony of the transformant obtained in (1.2) was recovered and this was inoculated to LB liquid culture medium (5 mL) containing 50 μg/mL ampicillin and culture was carried out in a test tube for approximately 22 hours at approximately 30° C. The culture (1.6 mL) was added to liquid culture medium (1.6 L) (1% glycerol-containing 6% Overnight Express™ Instant TB Medium (Merck), 0.1% A Adekanol LG-109 (ADEKA Corporation)) containing 50 μg/mL ampicillin, and culture was performed for approximately 24 hours using a jar fermenter and conditions of 30° C., 1.6 L/min aeration, and 650 rpm. The culture was submitted to centrifugal separation to collect the bacteria; the obtained bacterial cells were suspended in a solution A (20 mM potassium phosphate buffer (pH 7.0), 0.3 M NaCl); solubilization was carried out by ultrasonic disruption of the bacterial cells; and centrifugal separation was then performed to obtain a crude enzyme solution.

(2.2) Purification of HPT-W

Chelating Sepharose Fast Flow (GE Healthcare) was filled into a column, Ni$^{2+}$ was immobilized, and equilibration was subsequently carried out with solution A. The aforementioned crude enzyme solution was added to the resulting column and the HPT-W was adsorbed. The column was washed with solution A, and the HPT-W was then eluted with a linear gradient of 10 CVs (column volumes) using solution A and solution A containing 0.4 M imidazole. The resulting fraction with HPT-W activity was concentrated to one-tenth with a pencil module (UF) (Asahi Kasei Chemical Corporation), and desalting was performed using a PD-10 column (GE Healthcare) equilibrated with 10 mM potassium phosphate buffer (pH 7.0) to obtain an HPT-W enzyme solution.

(3) Preparation of HPT-C and HPT-L (3.1) Preparation of Hungateiclostridium Thermocellum-Derived HGPRT (HPT-C)

Transformant preparation, induction of HGPRT expression, and purification were carried out as for HPT-W, but carrying out PCR using as template an artificially synthesized gene that was a polynucleotide (SEQ ID NO: 8) that encoded Hungateiclostridium thermocellum-derived HGPRT (SEQ ID NO: 7), a sense primer (SEQ ID NO: 9), and an antisense primer (SEQ ID NO: 10), and carrying out insertion into the pET-21a(+) vector using the In-Fusion method, to obtain a solution of Hungateiclostridium thermocellum-derived HGPRT (HPT-C) having the His tag at the N terminal.

(3.2) Preparation of Archaeoglobus Veneficus-Derived HGPRT (HPT-L)

Transformant preparation, induction of HGPRT expression, and purification were carried out as for HPT-W, but carrying out PCR using as template an artificially synthesized gene that was a polynucleotide (SEQ ID NO: 12) that encoded Archaeoglobus veneficus-derived HGPRT (SEQ ID NO: 11), a sense primer (SEQ ID NO: 13), and an antisense primer (SEQ ID NO: 14), and carrying out insertion into the pET-21a(+) vector using the In-Fusion method, to obtain a solution of Archaeoglobus veneficus-derived HGPRT (HPT-L) having the His tag at the N terminal.

(4) Measurement of the Activity of the HPT-C, HPT-W, and HPT-L

The enzymatic activity of the HPT-C, HPT-W, and HPT-L for inosinic acid was measured based on the change in absorbance at 340 nm of the NADH produced by the conversion of the hypoxanthine produced by the action of the HGPRT to uric acid by xanthine dehydrogenase. 1 U was taken to be the amount of enzyme that produced 1 µmol of hypoxanthine in 1 minute at 37° C. The measurement was carried out using a Hitachi Model 7080 Automatic Analyzer (Hitachi High-Technologies Corporation). The composition of the activity measurement reagent, the composition of the enzyme diluent, and the measurement parameters for the Automatic Analyzer are as follows.

Composition of the Activity Measurement Reagent
20 mM Tris-HCl, pH 7.5 (Merck)
5 mM inosinic acid (Merck)
5 mM sodium diphosphate (FUJIFILM Wako Pure Chemical Corporation)
5 mM NAD (Oriental Yeast Co., Ltd.)
5 mM MgCl$_2$ (FUJIFILM Wako Pure Chemical Corporation)
5 U/mL XDH II (xanthine dehydrogenase: T-134, Asahi Kasei Pharma Corporation)

Composition of Enzyme Diluent
20 mM Tris-HCl, pH 7.5 (Merck)

Measurement Parameters for the Automatic Analyzer

| analytic method | Rate-A |
|---|---|
| measurement wavelengths (secondary/main) | 405 nm/340 nm |
| reaction time | 5 minutes |
| photometric points | 10-13 |
| sample size | 5 µL |
| amount of activity measurement reagent | 150 µL |

Example 3: Production of Base by HGPRT from Nucleoside Monophosphate and Pyrophosphate (First Step)

Preparation of Reaction Solutions

To prepare the reaction solutions, the following reagent components were dissolved with mixing in purified water to provide the indicated concentrations.

50 mM Tris-HCl (pH 8.0)
5 mM pyrophosphate
5 mM nucleoside monophosphate (IMP or GMP)
20 mM MgSO$_4$
2.5 U/mL HGPRT (HPT-C, HPT-W, or HPT-L)

Measurement

After reaction for 1 hour at 37° C., 20-fold dilution with purified water was carried out, filtration was performed with a membrane having a molecular weight cutoff of 10,000, and the filtrate was submitted to HPLC analysis.

Detection Conditions

Performed as in Example 1.

Results

The peak areas for IMP, hypoxanthine, GMP, and guanine are given in Table 2. It is shown that all three HGPRTs catalyze the reaction to hypoxanthine from IMP and to guanine from GMP.

TABLE 2

| enzyme | peak area | | peak area | |
|---|---|---|---|---|
| | IMP | hypoxanthine | GMP | guanine |
| Blank | 617573 | 0 | 840923 | 0 |
| HPT-C | 538668 | 5045 | 751979 | 2283 |
| HPT-W | 561871 | 1611 | 800388 | 2278 |
| HPT-L | 559140 | 4802 | 751686 | 7699 |

Example 4: Production of NMN from NAM and PRPP by HGPRT or NAMPT (Second Step)

Preparation of Reaction Solutions

To prepare the reaction solutions, the following reagent components were dissolved with mixing in purified water to provide the indicated concentrations.

100 mM of the particular buffer indicated in Table 3
2 mM NAM
2 mM PRPP
20 mM MgSO$_4$
2.5 U/mL HGPRT (HPT-C, HPT-W, or HPT-L) or 0.2 µg/mL NAMPT (SPR0514, Merck)

Measurement

After reaction for 2 hours at 37° C., 8-fold dilution with purified water was carried out, filtration was performed with a membrane having a molecular weight cutoff of 10,000, and the filtrate was submitted to HPLC analysis.

Detection Conditions

Performed as in Example 1.

Results

The peak areas for NMN and NAM are given in Table 3. It is shown that the reaction from NAM to NMN is catalyzed by HPT-C in the pH 5 and 6 buffers, by HPT-W in the pH 5, 6, 7, 8, and 9 buffers, by HPT-L in the pH 5 buffer, and by NAMPT in the pH 6, 7, 8, and 9 buffers.

TABLE 3

| enzyme | buffer | peak area NMN | peak area NAM |
|---|---|---|---|
| HPT-C | 100 mM acetate (pH 5) | 49014 | 172699 |
| | 100 mM MES (pH 6) | 4093 | 203140 |
| | 100 mM HEPES (pH 7) | 0 | 216188 |
| | 100 mM Tris (pH 8) | 0 | 217722 |
| | 100 mM Tris (pH 9) | 0 | 222149 |
| HPT-W | 100 mM acetate (pH 5) | 13990 | 209198 |
| | 100 mM MES (pH 6) | 10783 | 206558 |
| | 100 mM HEPES (pH 7) | 18996 | 205821 |
| | 100 mM Tris (pH 8) | 21042 | 207005 |
| | 100 mM Tris (pH 9) | 12475 | 220626 |
| HPT-L | 100 mM acetate (pH 5) | 3664 | 211200 |
| | 100 mM MES (pH 6) | 0 | 214716 |
| | 100 mM HEPES (pH 7) | 0 | 216426 |
| | 100 mM Tris (pH 8) | 0 | 220407 |
| | 100 mM Tris (pH 9) | 0 | 220045 |
| NAMPT | 100 mM acetate (pH 5) | 0 | 226731 |
| | 100 mM MES (pH 6) | 2305 | 230367 |
| | 100 mM HEPES (pH 7) | 2006 | 228549 |
| | 100 mM Tris (pH 8) | 7149 | 238620 |
| | 100 mM Tris (pH 9) | 3959 | 239065 |
| Blank | 100 mM acetate (pH 5) | 0 | 218602 |
| | 100 mM MES (pH 6) | 0 | 217792 |
| | 100 mM HEPES (pH 7) | 0 | 222457 |
| | 100 mM Tris (pH 8) | 0 | 222392 |
| | 100 mM Tris (pH 9) | 0 | 228221 |

Example 5: Production of Nucleoside Monophosphate from Base and PRPP by HGPRT (Reverse Reaction of the First Step)

Preparation of Reaction Solutions

To prepare the reaction solutions, the following reagent components were dissolved with mixing in purified water to provide the indicated concentrations.

50 mM Tris-HCl (pH 8.0)

1 mM base (hypoxanthine or guanine)

1 mM PRPP 5 mM $MgSO_4$ 2.5 U/mL HGPRT (HPT-C, HPT-W, or HPT-L)

Measurement

After reaction for 1 hour at 37° C., 4-fold dilution with purified water was carried out, filtration was performed with a membrane having a molecular weight cutoff of 10,000, and the filtrate was submitted to HPLC analysis.

Detection Conditions

Performed as in Example 1.

Results

The peak areas for IMP, hypoxanthine, GMP, and guanine are given in Table 4. It is shown that all three HGPRTs catalyze the reaction from hypoxanthine to IMP and from guanine to GMP.

TABLE 4

| enzyme | peak area IMP | peak area hypoxanthine | peak area GMP | peak area guanine |
|---|---|---|---|---|
| Blank | 0 | 1147260 | 0 | 35039 |
| HPT-C | 415172 | 203264 | 113852 | 9581 |
| HPT-W | 722619 | 284321 | 251250 | 0 |
| HPT-L | 554628 | 296415 | 67510 | 5962 |

Example 6: Production of NAM from NMN and Pyrophosphate by HGPRT or NAMPT (Reverse Reaction of the Second Step)

Preparation of Reaction Solutions

To prepare the reaction solutions, the following reagent components were dissolved with mixing in purified water to provide the indicated concentrations.

50 mM Tris-HCl (pH 8.0)

5 mM pyrophosphate 5 mM NMN 20 mM $MgSO_4$ 2.5 U/mL HGPRT (HPT-C, HPT-W, or HPT-L) or 0.2 µg/mL NAMPT (SPR0514, Merck)

Measurement

After reaction for 1 hour at 37° C., 20-fold dilution with purified water was carried out, filtration was performed with a membrane having a molecular weight cutoff of 10,000, and the filtrate was submitted to HPLC analysis.

Detection Conditions

Performed as in Example 1.

Results

The peak areas for NMN and NAM are given in Table 5. It is shown that NAMPT and all three HGPRTs catalyze the reaction from NMN to NAM.

TABLE 5

| enzyme | peak area NMN | peak area NAM |
|---|---|---|
| HPT-C | 0 | 204547 |
| HPT-W | 201439 | 68256 |
| HPT-L | 23167 | 189431 |
| NAMPT | 309532 | 8291 |
| Blank | 309316 | 7987 |

Example 7: Production of NMN by HGPRT from IMP, Pyrophosphate, and NAM (Simultaneous Execution of the First Step and the Second Step)

Preparation of Reaction Solutions

To prepare the reaction solutions, the following reagent components were dissolved with mixing in purified water to provide the indicated concentrations.

100 mM of the particular buffer indicated in Table 6

20 mM IMP 2 mM pyrophosphate 20 mM NAM 20 mM $MgSO_4$ 2.5 U/mL HGPRT (HPT-C or HPT-W)

Measurement

After reaction for 2 hours at 37° C., 40-fold dilution with purified water was carried out, filtration was performed with a membrane having a molecular weight cutoff of 10,000, and the filtrate was submitted to HPLC analysis.

Detection Conditions

Performed as in Example 1.

Results

The peak areas for NMN, NAM, IMP, and hypoxanthine are given in Table 6. It is shown that both HPT-C and HPT-W (except HPT-W at pH 6) catalyze the reactions to NMN from IMP, pyrophosphate, and NAM.

TABLE 6

| enzyme | buffer | peak area | | | |
|---|---|---|---|---|---|
| | | NMN | NAM | IMP | hypoxanthine |
| HPT-C | 100 mM acetate (pH 5) | 10842 | 441994 | 1324323 | 32877 |
| | 100 mM MES (pH 6) | 10099 | 455694 | 1407097 | 23613 |
| | 100 mM HEPES (pH 7) | 4306 | 439047 | 1420206 | 12312 |
| HPT-W | 100 mM acetate (pH 5) | 3750 | 426079 | 1318274 | 26331 |
| | 100 mM MES (pH 6) | 0 | 464308 | 1483465 | 5402 |
| | 100 mM HEPES (pH 7) | 1205 | 530231 | 1639925 | 5676 |

Example 8: Addition of XOD to the Reactions that Produce NMN Using HGPRT from IMP, Pyrophosphate, and NAM (Simultaneous Execution of the First Step and the Second Step)

Preparation of Reaction Solutions

To prepare the reaction solutions, the following reagent components were dissolved with mixing in purified water to provide the indicated concentrations.

100 mM of the particular buffer indicated in Table 7
5 mM IMP
5 mM pyrophosphate
5 mM NAM
20 mM MgSO₄
2.5 U/mL HPT-C(without XOD addition) or 2.5 U/mL HPT-C(with addition of 50 U/mL XOD (XTO-212, Toyobo Co., Ltd.))

Measurement

After reaction for 5 hours at 37° C., 20-fold dilution with purified water was carried out, filtration was performed with a membrane having a molecular weight cutoff of 10,000, and the filtrate was submitted to HPLC analysis.

Detection Conditions

Performed as in Example 1.

Results

The peak areas for NMN, NAM, IMP, and hypoxanthine are given in Table 7. It is shown that the reactions to NMN from IMP, pyrophosphate, and NAM are promoted by the addition of XOD.

TABLE 7

| buffer | XOD | peak area | | | |
|---|---|---|---|---|---|
| | | NMN | NAM | IMP | hypoxanthine |
| 100 mM acetate (pH 5) | − | 12856 | 219701 | 635981 | 32410 |
| | + | 41635 | 191834 | 373261 | 0 |
| 100 mM MES (pH 6) | − | 3437 | 216707 | 622639 | 15322 |
| | + | 31530 | 198469 | 353252 | 0 |
| 100 mM HEPES (pH 7) | − | 0 | 214882 | 640955 | 9747 |
| | + | 9972 | 211187 | 315997 | 0 |

Example 9: Addition of XOD to the Reactions that Produce NMN Using HGPRT from IMP, Pyrophosphate, and NAM (Simultaneous Execution of the First Step and the Second Step)

Preparation of Reaction Solutions

To prepare the reaction solutions, the following reagent components were dissolved with mixing in purified water to provide the indicated concentrations.

100 mM acetate (pH 5)
1 mM IMP
0.2 mM pyrophosphate
1 mM NAM
50 mM MgSO₄
2.5 U/mL HGPRT (HPT-C, HPT-W, or HPT-L)
10 U/mL XOD (XTO-212, Toyobo Co., Ltd.)

Measurement

After reaction for 1 hour at 37° C. or 65° C., 4-fold dilution with purified water was carried out, filtration was performed with a membrane having a molecular weight cutoff of 10,000, and the filtrate was submitted to HPLC analysis.

Detection Conditions

Performed as in Example 1.

Results

The peak areas for NMN, NAM, IMP, and hypoxanthine are given in Table 8. It is shown that HGPRT catalyzes the reactions to NMN from IMP, pyrophosphate, and NAM at 37° C. and 65° C.

TABLE 8

| enzyme | reaction temperature | peak area | | | |
|---|---|---|---|---|---|
| | | NMN | NAM | IMP | hypoxanthine |
| HPT-C | 37° C. | 32392 | 212714 | 415721 | 0 |
| HPT-W | 37° C. | 8978 | 224367 | 511594 | 0 |
| HPT-L | 37° C. | 22200 | 229345 | 341354 | 0 |
| HPT-C | 65° C. | 22978 | 244593 | 496055 | 20140 |

Example 10: Addition of XOD to the Reactions that Produce NMN Using HGPRT from a GMP+IMP Mixture, Pyrophosphate, and NAM (Simultaneous Execution of the First Step and the Second Step)

Preparation of Reaction Solutions

To prepare the reaction solutions, the following reagent components were dissolved with mixing in purified water to provide the indicated concentrations.

100 mM acetate (pH 5)
0.5 mM IMP
0.5 mM GMP
0.2 mM pyrophosphate
1 mM NAM
50 mM MgSO₄
2.5 U/mL HGPRT (HPT-C, HPT-W, or HPT-L)
10 U/mL XOD (XTO-212, Toyobo Co., Ltd.)

Measurement

After reaction for 1 hour at 37° C. or 65° C., 4-fold dilution with purified water was carried out, filtration was performed with a membrane having a molecular weight cutoff of 10,000, and the filtrate was submitted to HPLC analysis.

Detection Conditions
Performed as in Example 1.
Results
The peak areas for NMN, NAM, IMP, and GMP are given in Table 9. It is shown that HGPRT catalyzes the reactions to NMN from a GMP+IMP mixture, pyrophosphate, and NAM at 37° C. and 65° C.

TABLE 9

| enzyme | reaction temperature | peak area | | | |
|---|---|---|---|---|---|
| | | NMN | NAM | IMP | GMP |
| HPT-C | 37° C. | 32389 | 218194 | 235229 | 250537 |
| HPT-W | 37° C. | 9651 | 226081 | 217074 | 457382 |
| HPT-L | 37° C. | 19142 | 235352 | 229053 | 234700 |
| HPT-C | 65° C. | 18707 | 226718 | 234302 | 275248 |

Example 11: Addition of XOD to the Reactions that Produce NMN Using HGPRT from IMP, Pyrophosphate, and NAM, and Variation of the Ratios Among IMP, Pyrophosphate, and NAM (Simultaneous Execution of the First Step and the Second Step)

Preparation of Reaction Solutions
To prepare the reaction solutions, the following reagent components were dissolved with mixing in purified water to provide the indicated concentrations.
  100 mM acetate (pH 5)
  IMP, individual concentrations shown in Table 10
  pyrophosphate, individual concentrations shown in Table 10
  NAM, individual concentrations shown in Table 10
  50 mM MgSO₄
  2.5 U/mL HPT-C
  10 U/mL XOD (XTO-212, Toyobo Co., Ltd.)
Measurement
After reaction for 3 hours at 37° C., the 1 mM NAM reaction solution was diluted 4-fold with purified water, the 0.5 mM NAM reaction solution was diluted two-fold, and the 0.2 mM NAM reaction solution was not diluted; filtration was performed with a membrane having a molecular weight cutoff of 10,000; and the filtrate was submitted to HPLC analysis.
Detection Conditions
Performed as in Example 1.
Results
The peak areas for NMN, NAM, and IMP are given in Table 10. It is shown that NMN is produced at various ratios among the IMP, pyrophosphate, and NAM.

TABLE 10

| | | | peak area | | |
|---|---|---|---|---|---|
| IMP | pyrophosphate | NAM | NMN | NAM | IMP |
| 1 mM | 2 mM | 1 mM | 68726 | 213253 | 56779 |
| 1 mM | 1 mM | 1 mM | 60881 | 207177 | 100038 |
| 1 mM | 0.5 mM | 1 mM | 68454 | 201786 | 177238 |
| 1 mM | 0.2 mM | 1 mM | 63042 | 205302 | 291511 |
| 1 mM | 0.1 mM | 1 mM | 54516 | 208135 | 387533 |
| 1 mM | 0.02 mM | 1 mM | 31969 | 217933 | 555735 |
| 0.5 mM | 2 mM | 0.5 mM | 93909 | 217942 | 1817 |
| 0.5 mM | 1 mM | 0.5 mM | 85646 | 220533 | 13294 |
| 0.5 mM | 0.5 mM | 0.5 mM | 63555 | 214414 | 65660 |
| 0.5 mM | 0.2 mM | 0.5 mM | 36954 | 208263 | 169870 |
| 0.5 mM | 0.1 mM | 0.5 mM | 33517 | 225560 | 291861 |
| 0.5 mM | 0.02 mM | 0.5 mM | 15078 | 219722 | 461273 |
| 0.2 mM | 2 mM | 0.2 mM | 133155 | 189628 | 0 |
| 0.2 mM | 1 mM | 0.2 mM | 100517 | 191502 | 0 |
| 0.2 mM | 0.5 mM | 0.2 mM | 55757 | 180474 | 0 |
| 0.2 mM | 0.2 mM | 0.2 mM | 55116 | 182713 | 0 |
| 0.2 mM | 0.1 mM | 0.2 mM | 74748 | 180898 | 104288 |
| 0.2 mM | 0.02 mM | 0.2 mM | 49089 | 104679 | 166588 |

Example 12: Addition of XOD to the Reactions that Produce NMN Using HGPRT from GMP, Pyrophosphate, and NAM, and Variation of the Ratios Among GMP, Pyrophosphate, and NAM (Simultaneous Execution of the First Step and the Second Step)

Preparation of Reaction Solutions
To prepare the reaction solutions, the following reagent components were dissolved with mixing in purified water to provide the indicated concentrations.
  100 mM acetate (pH 5)
  1 mM GMP
  pyrophosphate, individual concentrations shown in Table 11
  1 mM NAM
  50 mM MgSO₄
  2.5 U/mL HPT-C
  10 U/mL XOD (XTO-212, Toyobo Co., Ltd.)
Measurement
After reaction for 6 hours at 37° C., the reaction solution was diluted 4-fold with purified water, filtration was performed with a membrane having a molecular weight cutoff of 10,000, and the filtrate was submitted to HPLC analysis.
Detection Conditions
Performed as in Example 1.
Results
The peak areas for NMN, NAM, and GMP are given in Table 11. It is shown that NMN is produced at various ratios among the GMP, pyrophosphate, and NAM.

TABLE 11

| | peak area | | |
|---|---|---|---|
| pyrophosphate | NMN | NAM | GMP |
| 2 mM | 1939 | 248562 | 776310 |
| 1 mM | 1670 | 251480 | 800076 |
| 0.5 mM | 2053 | 230718 | 750262 |

Example 13: Addition of XOD to the Reactions that Produce NMN Using HGPRT from IMP, Pyrophosphate, and NAM, and Changing the Mg Ion to the Mn Ion (Simultaneous Execution of the First Step and the Second Step)

Preparation of Reaction Solutions
To prepare the reaction solutions, the following reagent components were dissolved with mixing in purified water to provide the indicated concentrations.
  100 mM acetate (pH 5)
  1 mM IMP 0.2 mM pyrophosphate
1 mM NAM
50 mM MgSO₄ or 50 mM MnCl₂
2.5 U/mL HPT-C
10 U/mL XOD (XTO-212, Toyobo Co., Ltd.)
Measurement
After reaction for 3 hours at 37° C., the reaction solution was diluted 4-fold with purified water, filtration was performed with a membrane having a molecular weight cutoff of 10,000, and the filtrate was submitted to HPLC analysis.
Detection Conditions
Performed as in Example 1.
Results
The peak areas for NMN, NAM, and IMP are given in Table 12. It is shown that NMN is also produced when the Mn ion is used instead of the Mg ion.

TABLE 12

| metal ion | peak area | | |
| --- | --- | --- | --- |
| | NMN | NAM | IMP |
| MgSO₄ | 47596 | 215209 | 307010 |
| MnCl₂ | 40689 | 206148 | 404168 |

Example 14: Check on the Molecular Weight and Structure of the Nicotinamide Mononucleotide Produced by HGPRT from Nucleoside Monophosphate, Pyrophosphate, and Nicotinamide Preparation of Reaction Solutions
To prepare the reaction solutions, the following reagent components were dissolved with mixing in purified water to provide the indicated concentrations.
100 mM acetate (pH 5)
1 mM IMP
0.2 mM pyrophosphate
1 mM NAM
50 mM MgSO₄
2.5 U/mL HPT-C
10 U/mL XOD (XTO-212, Toyobo Co., Ltd.)
Measurement
After reaction for 3 hours at 37° C., the reaction solution was diluted 4-fold with purified water, filtration was performed with a membrane having a molecular weight cutoff of 10,000, and LC-MS/MS analysis was run.

Figure 3:
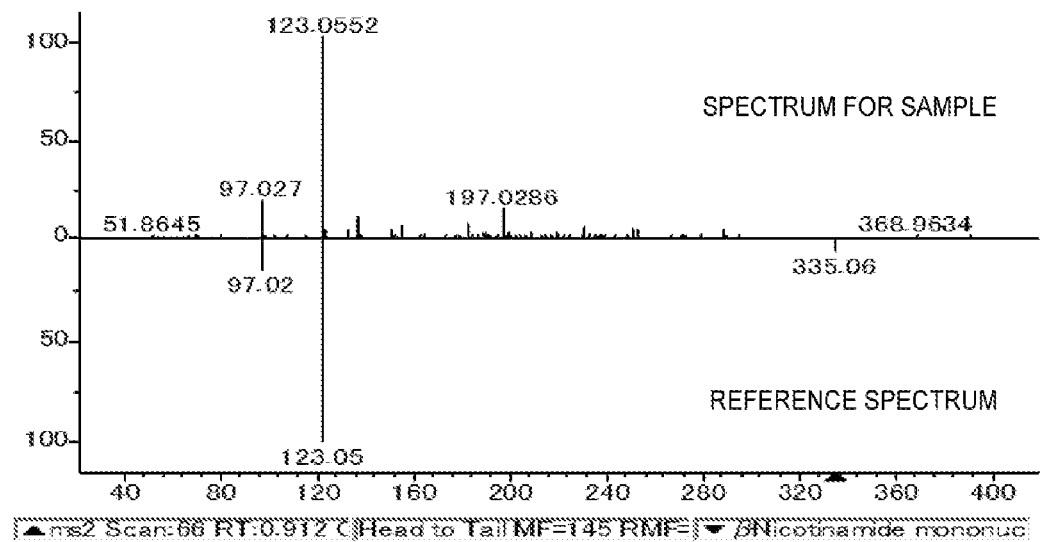
FIG. 3 is a diagram that shows the MS/MS spectra of NMN and the sample in Example 14.

Analytic Conditions
LC system: ACQUITY UPLC I-Class, Nihon Waters K.K.
MS: micrOTOF-Q III, Bruker Daltonics
  measurement conditions
  source type: ESI
  scan range: 50 to 1,000 m/z
  ion polarity: positive
  capillary: 4,500 V
  end plate: 500 V
  nebulizer: 1.2 bar
  dry heater: 200° C.
  dry gas: 6.0 L/min
software: DataAnalysis Ver. 4.3, Bruker Daltonics
  NIST MS Search Ver. 2.2, National Institute of Standards and Technology (USA)
column: ACQUITY UPLC BEH C18 2.1 mm I.D.×50 mm, 1.7 μm
column temperature: constant temperature in the vicinity of 40° C.
mobile phase: 10 mmol/L ammonium formate solution (pH 4.6)
flow rate: 0.2 mL/min
sample injection: 5 or 20 μL
Results
The substance (sample) produced in these reactions and eluting at the same retention time as NMN has a measured molecular weight value $[M+H]^+$ of 335.0637 and can be confirmed to agree with NMN in the MS/MS spectrum given in FIG. 3.
Sequence Listing Free Text
SEQ ID NO: 1: sense primer used in (1.1) of Example 2
SEQ ID NO: 2: antisense primer used in (1.1) of Example 2
SEQ ID NO: 3: base sequence of gene coding for HPT-W
SEQ ID NO: 4: amino acid sequence of HPT-W
SEQ ID NO: 5: sense primer used in (1.2) of Example 2
SEQ ID NO: 6: antisense primer used in (1.2) of Example 2
SEQ ID NO: 7: amino acid sequence of HPT-C
SEQ ID NO: 8: base sequence of gene coding for HPT-C
SEQ ID NO: 9: sense primer used in (3.1) of Example 2
SEQ ID NO: 10: antisense primer used in (3.1) of Example 2
SEQ ID NO: 11: amino acid sequence of HPT-L
SEQ ID NO: 12: base sequence of gene coding for HPT-L
SEQ ID NO: 13: sense primer used in (3.2) of Example 2
SEQ ID NO: 14: antisense primer used in (3.2) of Example 2
Sequence Listing

What is claimed is:

1. A method for making nicotinamide mononucleotide (NMN), which method comprises at least the following steps 1) and 2):
   1) Reacting a hypoxanthine phosphoribosyltransferase (HPT, EC 2.4.2.8) in a reaction mixture with a nucleoside monophosphate at a concentration of 0.01-500 mM and pyrophosphate at a concentration of 0.001-100 mM to produce phosphoribosyl diphosphate (PRPP); and
   2) Reacting said HPT in the reaction mixture with said PRPP and nicotinamide to produce nicotinamide mononucleotide (NMN) at a concentration of 0.01-500 mM;
   wherein said nucleoside monophosphate is at least one member selected from the group consisting of adenosine monophosphate (AMP), 5'-guanylic acid (GMP), inosinic acid (IMP) and xanthosine monophosphate (XMP), said HPT is present in said reaction mixture in an amount of 0.01 U-1000 kU/L and said HPT is present in an amount of at least 90% of any enzymes present in said reaction mixture, wherein said at least 90% indicates enzyme protein weight or a unit of activity for the enzyme.

2. The method according to claim 1, wherein said steps 1) and 2) are carried out simultaneously in the same reaction mixture.

3. The method according to claim 1, wherein said reaction mixture comprises at least one member selected from the group consisting of a buffer, an enzyme stabilizer and a surfactant.

4. The method according to claim 2, wherein said reaction mixture comprises at least one member selected from the group consisting of a buffer, an enzyme stabilizer and a surfactant.

5. The method according to claim 1, wherein said HPT is at least one member selected from the group consisting of HPT-C(enzyme comprising the amino acid sequence given by SEQ ID NO: 7), HPT-W (enzyme comprising the amino acid sequence given by SEQ ID NO: 4), HPT-L (enzyme comprising the amino acid sequence given by SEQ ID NO: 11), and a polypeptide that contains an amino acid sequence that has at least 90% sequence identity with the amino acid sequence of any one of HPT-C, HPT-W, and HPT-L.

6. The method according to claim 1, wherein said nucleoside monophosphate is IMP, GMP, or a mixture of IMP and GMP.

7. The method according to claim 1, wherein all or a portion of said nucleoside monophosphate is IMP, and
   said step 1) includes a step of causing an action of xanthine oxidase on hypoxanthine produced in said step 1).

8. The method according to claim 1, wherein said reaction mixture further comprises Mg ion and/or Mn ion.

9. A method for producing nicotinamide mononucleotide (NMN), which method comprises:
   reacting at least one hypoxanthine phosphoribosyltransferase (HPT, EC 2.4.2.8) in a reaction mixture with phosphoribosyl diphosphate (PRPP) and nicotinamide to produce nicotinamide mononucleotide (NMN) at a concentration of 0.01-500 mM;
   wherein said HPT is present in said reaction mixture in an amount of 0.01 U-1000 kU/L and said HPT is present in an amount of at least 90% of any enzymes present in said reaction mixture, wherein said at least 90% indicates enzyme protein weight or a unit of activity for the enzyme.

10. The method according to claim 9, wherein said HPT is at least one member selected from the group consisting of HPT-C(enzyme comprising the amino acid sequence given by SEQ ID NO: 7), HPT-W (enzyme comprising the amino acid sequence given by SEQ ID NO: 4), HPT-L (enzyme comprising the amino acid sequence given by SEQ ID NO: 11), and a polypeptide that contains an amino acid sequence that has at least 90% sequence identity with the amino acid sequence of any one of HPT-C, HPT-W, and HPT-L.

11. The method according to claim 9, wherein said reaction mixture further comprises Mg ion and/or Mn ion.

* * * * *

SEQUENCE LISTING

```
Sequence total quantity: 17
SEQ ID NO: 1           moltype = DNA  length = 24
FEATURE                Location/Qualifiers
misc_feature           1..24
                       note = Sense primer used in (1.1) of Example 2
source                 1..24
                       mol_type = other DNA
                       organism = synthetic construct
SEQUENCE: 1
ttactggtat actgcgtgtc ttgc                                          24

SEQ ID NO: 2           moltype = DNA  length = 24
FEATURE                Location/Qualifiers
misc_feature           1..24
                       note = Antisense primer used in (1.1) of Example 2
source                 1..24
```

```
                              mol_type = other DNA
                              organism = synthetic construct
SEQUENCE: 2
ttccaacctc aagctgaaac acgc                                          24

SEQ ID NO: 3                  moltype = DNA   length = 537
FEATURE                       Location/Qualifiers
misc_feature                  1..537
                              note = Nucleotide sequence of the gene encoding HPT-W
source                        1..537
                              mol_type = genomic DNA
                              organism = Escherichia coli
SEQUENCE: 3
atgaaacata ctgtagaagt aatgatcccc gaagcggaga ttaaagcgcg tatcgccgaa   60
ctgggtcgtc agattactga gcgttacaaa gacagcggca gcgatatggt gctggtgggt  120
ctgctgcgtg gctcatttat gtttatggcg gacctgtgcc gtgaagttca ggtatctcat  180
gaagtcgact ttatgaccgc ctccagctac ggtagcggca tgtccaccac ccgtgatgtg  240
aaaatcctca aagatctgga tgaagatatc cgtggcaagg acgtgctgat tgttgaagat  300
atcatcgact cggggaatac actgtcgaaa gtgcgtgaga tcttaagcct gcgcgaaccg  360
aagtcgctgg cgatttgtac gctgctggat aaaccgtccc gtcgtgaagt gaacgtcccg  420
gtagaattta tcgtttctct gatcccggat gagtttgtgg tgggttacgg cattgattac  480
gcacagcgtt accgtcatct gccgtatatc ggcaaagtga ttctgctgga cgagtaa     537

SEQ ID NO: 4                  moltype = AA   length = 178
FEATURE                       Location/Qualifiers
REGION                        1..178
                              note = MISC_FEATURE - Amino acid sequence of HPT-W
source                        1..178
                              mol_type = protein
                              organism = Escherichia coli
SEQUENCE: 4
MKHTVEVMIP EAEIKARIAE LGRQITERYK DSGSDMVLVG LLRGSFMFMA DLCREVQVSH   60
EVDFMTASSY GSGMSTTRDV KILKDLDEDI RGKDVLIVED IIDSGNTLSK VREILSLREP  120
KSLAICTLLD KPSRREVNVP VEFIGFSIPD EFVVGYGIDY AQRYRHLPYI GKVILLDE    178

SEQ ID NO: 5                  moltype = DNA   length = 60
FEATURE                       Location/Qualifiers
misc_feature                  1..60
                              note = Sense primer used in (1.2) of Example 2
source                        1..60
                              mol_type = other DNA
                              organism = synthetic construct
SEQUENCE: 5
aaggagatat acatatgcat caccatcacc atcacaaaca tactgtagaa gtaatgatcc   60

SEQ ID NO: 6                  moltype = DNA   length = 40
FEATURE                       Location/Qualifiers
misc_feature                  1..40
                              note = Antisense primer used in (1.2) of Example 2
source                        1..40
                              mol_type = other DNA
                              organism = synthetic construct
SEQUENCE: 6
gctcgaattc ggatcttact cgtccagcag aatcactttg                         40

SEQ ID NO: 7                  moltype = AA   length = 184
FEATURE                       Location/Qualifiers
REGION                        1..184
                              note = MISC_FEATURE - Amino acid sequence of HPT-C
source                        1..184
                              mol_type = protein
                              organism = Hungateiclostridium thermocellum
SEQUENCE: 7
MINQIKEILV TREELKNNAK ELGKRISSDY EGKELVLIGV LKGGVVFFAD LIREITIPID   60
VDFISVSSYG NSTKSSGVVR IIKDIDIDIT NKHVLIVEDL VDTGLTLHYL KSMFEARGPK  120
DVKICTALDK PSRRKVDLEI DYKGITIPDK FVVGYGLDYA EKYRNLPDVC VLDSSVYTDK  180
EDMD                                                               184

SEQ ID NO: 8                  moltype = DNA   length = 555
FEATURE                       Location/Qualifiers
misc_feature                  1..555
                              note = Nucleotide sequence of the gene encoding HPT-C
source                        1..555
                              mol_type = genomic DNA
                              organism = Hungateiclostridium thermocellum
SEQUENCE: 8
atgatcaacc agattaagga gatcctggtg acccgtgagg aactgaagaa caacgcgaaa   60
gaactgggca gcgtattag cagcgattat gagggtaaag aactggtgct gatcggcgtt  120
ctgaagggtg gcgtggtttt ctttgcggac ctgattcgtg agatcaccat tccgatcgac  180
```

-continued

```
gtggatttca tcagcgttag cagctacggt aacagcacca aaagcagcgg cgtggttcgt    240
atcattaagg acattgatat cgacattacc aacaaacacg tgctgatcgt tgaggatctg    300
gtggacaccg gtctgaccct gcactatctg aaaagcatgt tcgaagcgcg tggcccgaag    360
gatgtgaaaa tttgcaccgc gctggacaaa ccgagccgtc gtaaggttga tctggaaatc    420
gactacaaag gcatcaccat tccggataag tttgtggttg gttacggcct ggactatgcg    480
gagaagtacc gtaacctgcc ggatgtgtgc gttctggaca gcagcgttta taccgataaa    540
gaagatatgg actaa                                                      555

SEQ ID NO: 9           moltype = DNA  length = 60
FEATURE                Location/Qualifiers
misc_feature           1..60
                       note = Sense primer used in (3.1) of Example 2
source                 1..60
                       mol_type = other DNA
                       organism = synthetic construct
SEQUENCE: 9
aaggagatat acatatgcat caccatcacc atcacatcaa ccagattaag gagatcctgg    60

SEQ ID NO: 10          moltype = DNA  length = 40
FEATURE                Location/Qualifiers
misc_feature           1..40
                       note = Antisense primer used in (3.1) of Example 2
source                 1..40
                       mol_type = other DNA
                       organism = synthetic construct
SEQUENCE: 10
gctcgaattc ggatcttagt ccatatcttc tttatcggta                           40

SEQ ID NO: 11          moltype = AA  length = 174
FEATURE                Location/Qualifiers
REGION                 1..174
                       note = MISC_FEATURE - Amino acid sequence of HPT-L
source                 1..174
                       mol_type = protein
                       organism = Archaeoglobus veneficus
SEQUENCE: 11
MELELLIGGE EIRGRVKELA EQISKDYRDR IGDETPLLIG ILNGAFIFLA DLIRELSIPV    60
EVDFVKLKSY VGTNSTGTVE VKLDVEREIE GRDVIVVEDI IDTGITMEFF LNRLKKKKPK   120
SIAVCTLLDK PERRIVDVKP DYVGFTIPDY FVVGYGLDFN GRYRELPAIY RVKP          174

SEQ ID NO: 12          moltype = DNA  length = 525
FEATURE                Location/Qualifiers
misc_feature           1..525
                       note = Nucleotide sequence of the gene encoding HPT-L
source                 1..525
                       mol_type = genomic DNA
                       organism = Archaeoglobus veneficus
SEQUENCE: 12
atggagctgg aactgctgat cggtggcgag gaaattcgtg gtcgtgtgaa ggaactggcg    60
gagcagatca gcaaagacta ccgtgatcgt attggcgacg aaaccccgct gctgatcggt   120
attctgaacg gcgcgttcat cttcctggcg gacctgatcc gtgaactgag cattccggtg   180
gaggttgatt tcgtgaagct gaaaagctat gttggtacca acagcaccgg caccgtggag   240
gttaagctgg acgtggagcg tgaaatcgag ggtcgtgatg ttattgtggt tgaagacatc   300
attgataccg gcatcaccat ggagttcttt ctgaaccgtc tgaagaaaaa gaaaccgaaa   360
agcattgcgg tgtgcaccct gctggataag ccggaacgtc gtatcgtgga cgttaaaccg   420
gattacgttg gtttcaccat tccggactac tttgtggttg gttatggcct ggattttaac   480
ggccgttacc gtgagctgcc ggcgatctat cgtgttaagc cgtaa                   525

SEQ ID NO: 13          moltype = DNA  length = 60
FEATURE                Location/Qualifiers
misc_feature           1..60
                       note = Sense primer used in (3.2) of Example 2
source                 1..60
                       mol_type = other DNA
                       organism = synthetic construct
SEQUENCE: 13
aaggagatat acatatgcat caccatcacc atcacgagct ggaactgctg atcggtggcg    60

SEQ ID NO: 14          moltype = DNA  length = 40
FEATURE                Location/Qualifiers
misc_feature           1..40
                       note = Antisense primer used in (3.2) of Example 2
source                 1..40
                       mol_type = other DNA
                       organism = synthetic construct
SEQUENCE: 14
gctcgaattc ggatcttacg gcttaacacg atagatcgcc                           40

SEQ ID NO: 15          moltype = DNA  length = 14
```

```
FEATURE            Location/Qualifiers
misc_feature       1..14
                   note = Synthetic
source             1..14
                   mol_type = other DNA
                   organism = synthetic construct
SEQUENCE: 15
aaggagatat acat                                                        14

SEQ ID NO: 16      moltype = DNA  length = 18
FEATURE            Location/Qualifiers
misc_feature       1..18
                   note = Synthetic
source             1..18
                   mol_type = other DNA
                   organism = synthetic construct
SEQUENCE: 16
catcaccatc accatcac                                                    18

SEQ ID NO: 17      moltype = DNA  length = 16
FEATURE            Location/Qualifiers
misc_feature       1..16
                   note = Synthetic
source             1..16
                   mol_type = other DNA
                   organism = synthetic construct
SEQUENCE: 17
ggatccgaat tcgagc                                                      16
```